(12) United States Patent
Falkenberg et al.

(10) Patent No.: US 7,901,717 B1
(45) Date of Patent: Mar. 8, 2011

(54) ALKALIZING COMPOSITIONS AND METHODS FOR USING THE SAME

(75) Inventors: Ricky L. Falkenberg, Turlock, CA (US); Harold L. Archibald, Fairfield, CA (US); Danford Wilkinson, Benicia, CA (US); Lisa Trexler, Winchester, CA (US); Julie M. Hayes, Vacaville, CA (US)

(73) Assignee: Scientific Food Solutions, LLC, Fairfield, CA (US)

( * ) Notice: Subject to any disclaimer, the term of this patent is extended or adjusted under 35 U.S.C. 154(b) by 1188 days.

(21) Appl. No.: 11/539,621

(22) Filed: Oct. 6, 2006

Related U.S. Application Data (63) Continuation-in-part of application No. 11/457,839, filed on Jul. 17, 2006, now abandoned, and a continuation-in-part of application No. 11/424,869, filed on Jun. 17, 2006, application No. 11/539,621, which is a continuation-in-part of application No. 11/382,051, filed on May 7, 2006, now abandoned.

(60) Provisional application No. 60/595,258, filed on Jun. 20, 2005, provisional application No. 60/595,072, filed on Jun. 3, 2005.

(51) Int. Cl.
*A61K 36/8962* (2006.01)
*A61K 36/00* (2006.01)

(52) U.S. Cl. .......................................................... 424/754
(58) Field of Classification Search ........................ None
See application file for complete search history.

(56) References Cited

U.S. PATENT DOCUMENTS

| 3,720,672 | A | * | 3/1973 | Buttery et al. | ................. | 544/408 |
|---|---|---|---|---|---|---|
| 3,725,085 | A | * | 4/1973 | Schwimmer | ..................... | 426/63 |
| 5,260,090 | A | * | 11/1993 | Isao | ............................. | 426/638 |
| 6,548,100 | B1 | * | 4/2003 | Bauer et al. | ..................... | 426/589 |
| 2004/0033295 | A1 | * | 2/2004 | Gimelli et al. | ................ | 426/120 |
| 2004/0037879 | A1 | * | 2/2004 | Adusumilli et al. | ........... | 424/468 |
| 2006/0073189 | A1 | * | 4/2006 | Pinney et al. | ................. | 424/440 |

* cited by examiner

*Primary Examiner* — Christopher R. Tate
(74) *Attorney, Agent, or Firm* — Jeffer Mangels Butler & Mitchell LLP (57) ABSTRACT

An alkalizing composition comprising calcium carbonate, potassium hydroxide, potassium bicarbonate, and dicalcium phosphate. The alkalizing composition may further comprise any one or a combination of magnesium hydroxide, tricalcium phosphate, vitamin, a binder, sea minerals and water. The alkalizing compositions may be formulated as an antacid, a nutritional or dietary supplement, or a sports beverage. The alkalizing composition may be used in methods to buffer garlic. The buffered garlic compositions produced in accordance with the methods provides high allicin yield under acidic conditions. The alkalizing compositions may also be used in methods to enhance the flavor of fruits and vegetables.

10 Claims, 3 Drawing Sheets

Fig. 1

FIG. 2A. Concentration curve after consuming 4mg of fresh garlic

FIG. 2B. Concentration curve after consuming the Buffered Garlic Composition

Fig. 3

ALKALIZING COMPOSITIONS AND METHODS FOR USING THE SAME

CROSS REFERENCE TO RELATED APPLICATIONS

This application is a continuation-in-part of U.S. patent application Ser. No. 11/457,839, filed Jul. 17, 2006, which is hereby incorporated herein by reference. This application is also a continuation-in-part of U.S. patent application Ser. No. 11/424,869, filed Jun. 17, 2006, which claims the benefit of U.S. Provisional Application No. 60/595,258, filed Jun. 20, 2005, all of which is hereby incorporated herein by reference. This application is also a continuation-in-part of U.S. patent application Ser. No. 11/382,051, filed May 7, 2006, which claims the benefit of U.S. Provisional Application No. 60/595,072, filed Jun. 3, 2005, all of which is hereby incorporated herein by reference.

FIELD OF THE INVENTION

The present invention relates generally to alkalizing compositions and methods for using the same.

BACKGROUND OF THE INVENTION

Studies have shown that the consumption of raw garlic provides numerous health benefits as an antihyperlipidemic, antimicrobial, antiplatelet, antioxidant, anti-diabetic, and as a vasoprotective agent.

Allicin is widely believed to be the pharmacologically active component responsible for many of these beneficial health effects of garlic consumption. Allicin is produced by an enzymatic reaction of allinase and alliin. The allinase enzyme is stored in a separate area from the alliin within the garlic and combines with alliin in raw garlic when the garlic is crushed or macerated to produce allicin. Because allicin is unstable, it readily converts to other compounds once it is formed. Therefore cooking, aging, crushing and otherwise processing garlic causes allicin to be converted into other compounds.

Although the consumption of raw garlic provides high allicin yields, it is also associated with a number of undesirable side effects, such as halitosis, body odor, and gastrointestinal disturbances. As a result, efforts have been made to develop a garlic supplement that provides the beneficial health effects of raw garlic without the undesirable side effects associated with its consumption.

Studies have shown, however, that many of the garlic supplements currently available release far less allicin under simulated gastrointestinal conditions. The difficulty in releasing allicin from garlic supplements is related to the fact that allicin is not present in uncrushed garlic or in garlic powder but is produced by the interaction between the allinase and aliin.

To prevent the decomposition of allinase by stomach acid, some manufacturers have enteric-coated garlic powders in order to bypass the stomach. However, simulated intestinal fluids have been shown to significantly reduce, or even completely destroy, allicin production even in enteric-coated garlic preparations. Moreover, allinase, the enzyme which catalyzes the conversion of alliin to allicin, has been shown to be irreversibly deactivated at pH 3 or below, an acidic environment typically found in the stomach.

BRIEF SUMMARY OF THE PREFERRED EMBODIMENTS

Disclosed herein are alkalizing compositions and methods for using the alkalizing composition in connection with the preparation of food, beverages, antacids, and dietary and nutritional supplements.

In one preferred embodiment, the alkalizing composition comprises calcium carbonate, potassium hydroxide, potassium bicarbonate, and dicalcium phosphate.

In one aspect of this preferred embodiment, the alkalizing composition may comprise from about 50% to about 99% by weight calcium carbonate, from about 0.01% to about 8% by weight potassium hydroxide, from about 0.01% to about 10% by weight potassium bicarbonate, and from about 0.01% to about 5% by weight dicalcium phosphate.

In another aspect of this preferred embodiment, the alkalizing composition may be provided in an aqueous solution. In accordance with this aspect, the alkalizing composition may comprise from about 70% to about 99% by weight water, from about 10% to about 40% by weight calcium carbonate, from about 0.01% to about 10% by weight potassium hydroxide, from about 0.01% to about 10% by weight potassium bicarbonate, and from about 0.01% to about 10% by weight dicalcium phosphate.

In yet another aspect of this preferred embodiment, the alkalizing composition may comprise any one or a combination of the following: sodium hydroxide, magnesium hydroxide, tricalcium phosphate, a vitamin, such as ascorbic acid and/or vitamin $D_3$, and a binder, such as gum acacia.

In accordance with this aspect of this preferred embodiment, the alkalizing composition may comprise from about 50% to about 99% by weight calcium carbonate, from about 0.01% to about 10% by weight sodium hydroxide, from about 0.01% to about 10% by weight dicalcium phosphate, from about 0.01% to about 10% by weight potassium hydroxide, from about 0.01% to about 10% by weight potassium bicarbonate, from about 0.01% to about 10% by weight gum acacia.

In accordance with another aspect of this preferred embodiment, the alkalizing composition may comprise from about 50% to about 99% by weight calcium carbonate, from about 0.01% to about 10% by weight potassium hydroxide, from about 0.01% to about 10% by weight dicalcium phosphate, from about 0.01% to about 10% by weight tricalcium phosphate, and from about 0.01% to about 10% by weight potassium bicarbonate.

In accordance with yet another aspect of this preferred embodiment, the alkalizing composition may comprise from about 50% to about 99% by weight calcium carbonate, from about 0.01% to about 10% by weight magnesium hydroxide, from about 0.01% to about 10% by weight dicalcium phosphate, from about 0.01% to about 10% by weight potassium hydroxide, from about 0.01% to about 10% by weight potassium bicarbonate, from about 0.01% to about 10% by weight gum acacia. This composition may optionally comprise a vitamin, such as ascorbic acid in an amount from about 0.01% to about 10% by weight.

In another preferred embodiment, the alkalizing composition comprises calcium carbonate, magnesium hydroxide, a vitamin, and potassium hydroxide. The vitamin may be selected from any number of vitamins suitable for ingestion, including but not limited to ascorbic acid and vitamin $D_3$.

In one aspect of this preferred embodiment, the alkalizing composition may comprise any one or a combination of the following: dicalcium phosphate and a binder, such as gum acacia.

In accordance with this aspect of the preferred embodiment, the alkalizing composition may comprise from about 50% to about 99% by weight calcium carbonate, from about 0.01% to about 10% by weight magnesium hydroxide, from about 0.01% to about 10% by weight ascorbic acid, from about 0.01% to about 10% by weight gum acacia, and from about 0.01% to about 8% by weight potassium hydroxide. The alkalizing composition may further comprise from about 0.01% to about 10% by weight dicalcium phosphate.

In accordance with yet another aspect of the preferred embodiment, buffered garlic compositions are provided. The buffered garlic composition comprises calcium carbonate, potassium hydroxide, potassium bicarbonate, and dicalcium phosphate. The garlic may be in the form of fresh garlic or dried garlic powder, and preferably contains a high allicin content. The buffered garlic compositions may further comprise any one or a combination of magnesium hydroxide and sodium hydroxide.

In accordance with one aspect of this preferred embodiment, the buffered garlic composition comprises from about 50% to about 99% by weight garlic, from about 1% to about 40% by weight calcium carbonate, from about 0.01% to about 10% by weight potassium hydroxide, from about 0.01% to about 10% by weight magnesium hydroxide, from about 0.01% to about 10% by weight potassium bicarbonate, and from about 0.01% to about 10% by weight dicalcium phosphate.

In accordance with another aspect of this preferred embodiment, the buffered garlic composition comprises from about 50% to about 99% by weight garlic, from about 1% to about 40% by weight calcium carbonate, from about 0.01% to about 10% by weight potassium hydroxide, from about 0.01% to about 10% by weight sodium hydroxide, from about 0.01% to about 10% by weight potassium bicarbonate, and from about 0.01% to about 10% by weight dicalcium phosphate.

In accordance with yet another aspect of this preferred embodiment, the buffered garlic composition comprises from about 1% to about 40% by weight garlic, from about 40% to about 90% by weight calcium carbonate, from about 0.01% to about 10% by weight potassium hydroxide, from about 0.01% to about 10% by weight magnesium hydroxide, from about 0.01% to about 10% by weight potassium bicarbonate, and from about 0.01% to about 10% by weight dicalcium phosphate.

In a further preferred embodiment, methods for buffering garlic are provided. The method comprises the steps of providing garlic and applying an alkalizing solution to the garlic. The alkalizing solution may preferably be about 0.001% to about 5% by weight in water.

In one aspect of this preferred embodiment, the alkalizing solution comprises water, calcium carbonate and potassium hydroxide. The alkalizing solution may further comprise any one or a combination of magnesium hydroxide, potassium bicarbonate, dicalcium phosphate, a vitamin, such as ascorbic acid or vitamin $D_3$, and a binder, such as gum acacia.

In still a further preferred embodiment, methods for buffering garlic are provided. The method comprises the steps of providing garlic; rinsing the garlic in an acidic solution, preferably aqueous solution of paracetic acid; rinsing the garlic in chlorinated water; applying an acidic solution, preferably aqueous citric acid solution to the garlic; and applying an alkalizing solution to the sliced garlic. The alkalizing composition may further comprise any one or a combination of magnesium hydroxide and potassium bicarbonate.

In another preferred embodiment, a method for manufacturing a buffered garlic composition is provided. The method comprises the steps of providing garlic powder; providing an alkalizing composition; and dry blending the garlic powder and the alkalizing composition.

In one aspect of this preferred embodiment, the alkalizing composition may comprise calcium carbonate, potassium hydroxide, potassium bicarbonate, and dicalcium phosphate. In another aspect of this preferred embodiment, the alkalizing composition may further comprise any one or a combination of calcium carbonate, magnesium hydroxide, gum acacia, ascorbic acid, dicalcium phosphate, potassium bicarbonate, and potassium hydroxide.

In a further preferred embodiment, a method for enhancing the flavors of fruits and vegetables is provided. The method comprises applying an alkalizing solution to the fruits and vegetables; at least partially drying the fruits and vegetables; and at least partially freezing the fruits and vegetables. In one aspect, the fruits and vegetables are frozen solid.

In one aspect of this preferred embodiment, the alkalizing composition comprises calcium carbonate, magnesium hydroxide, a vitamin, such as ascorbic acid or vitamin $D_3$, a binder, such as gum acacia, and potassium hydroxide. The alkalizing composition may further comprise dicalcium phosphate.

In a yet a further preferred embodiment, a beverage containing the alkalizing composition is provided. The beverage comprises water, calcium carbonate, concentrated sea minerals, magnesium hydroxide, potassium hydroxide, and dicalcium phosphate.

In accordance with one aspect of this preferred embodiment, the beverage comprises from about 50% to about 99% by weight water, from about 10% to about 30% by weight calcium carbonate, from about 0.01% to about 10% by weight concentrated sea minerals, from about 0.01% to about 10% by weight magnesium hydroxide, from about 0.01% to about 10% by weight potassium hydroxide, and from about 0.01% to about 10% by weight by weight dicalcium phosphate.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

The invention may be more readily understood by referring to the accompanying drawings in which.

DETAILED DESCRIPTION OF THE PREFERRED EMBODIMENTS

The alkalizing compositions disclosed herein may be provided in any number of forms suitable for ingestion, including but not limited to powders, granules, tablets, capsules, suspensions, liquids, solutions, emulsions, and any other form known to one of ordinary skill in the art.

In one preferred embodiment, the alkalizing compositions may be formulated as a dietary or nutritional supplement to provide vitamins and minerals.

In another preferred embodiment, the alkalizing compositions may be formulated as an antacid to treat disorders which relate to body's production of excess gastric acid, such as acid indigestion, acid reflux, GERD, irritable bowel syndrome, and gout.

Figure 1:
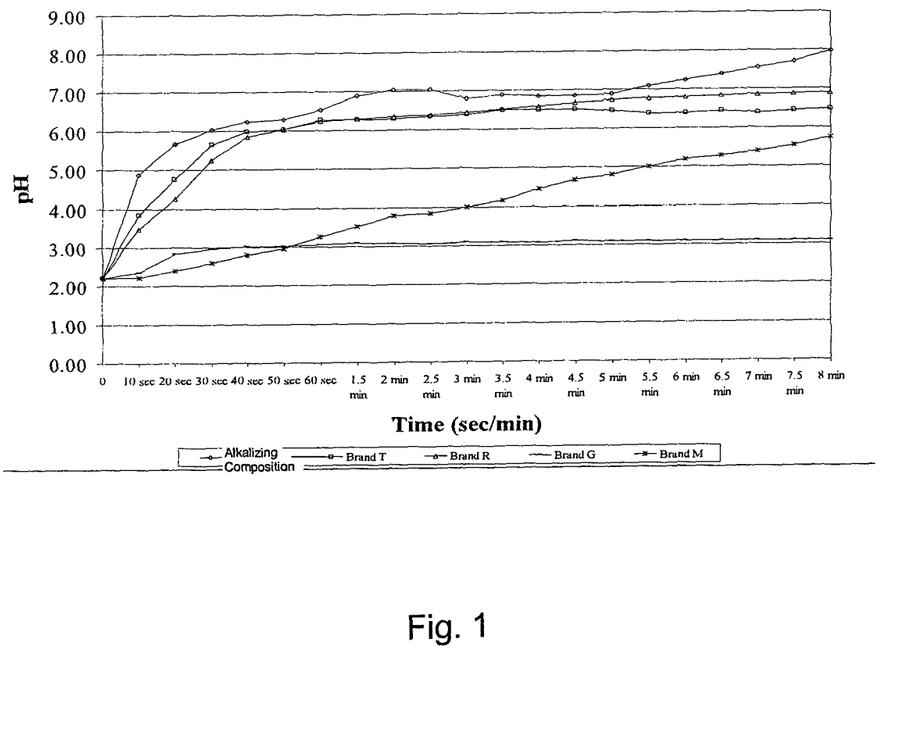
FIG. 1 compares the antacid effectiveness of the alkalizing composition with known antacid brands as a function of neutralization of 0.017M HCl (pH 2.0).

FIG. 1 shows the effectiveness of the alkalizing composition as an antacid as compared to known and commercially available antacid formulations.

The alkalizing compositions may also be formulated as an electrolytic beverage that is consumed after strenuous physical activity to replenish the electrolytes in the body, to invigorate tired or sore muscles, and to reduce gastric distress resulting from excess stomach acid.

In one preferred embodiment, the electrolytic beverage comprises deionized water, calcium carbonate, concentrated sea mineral, magnesium hydroxide, potassium hydroxide, and dicalcium phosphate.

The pH of the electrolytic beverage is in the range of from about 6.0 to about 10.0, preferably 7.0 to about 9.0, and more preferably from about 8.0 to about 9.0.

The electrolytic beverage may optionally contain from about 0.01% to about 1% by weight vitamin $D_3$ to help the absorption of the minerals and electrolytes into the body.

The alkalizing compositions disclosed herein may also be used in processes for buffering fresh or dried garlic and in processes for enhancing the flavor of fruits and vegetables.

Figure 2A:
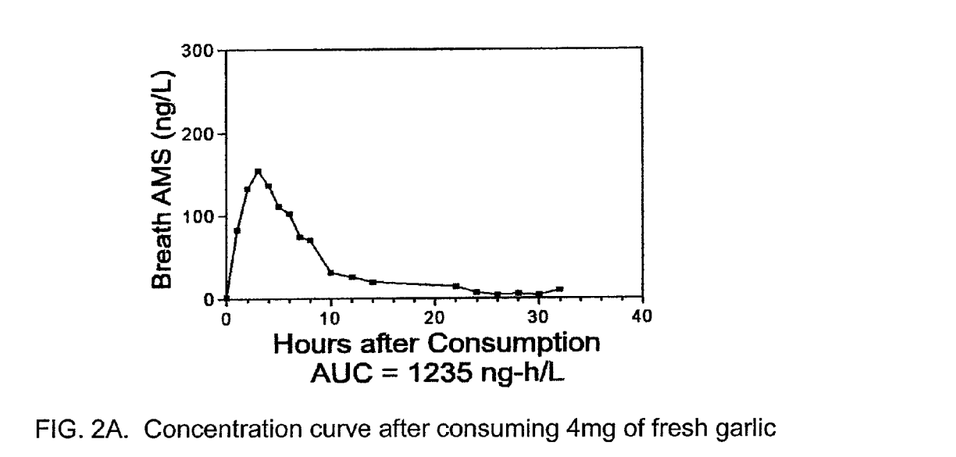
FIGS. 2A and 2B show the allicin bioavailability from fresh garlic and the allicin bioavailability from the buffered garlic compositions, respectively.
Figure 2B:
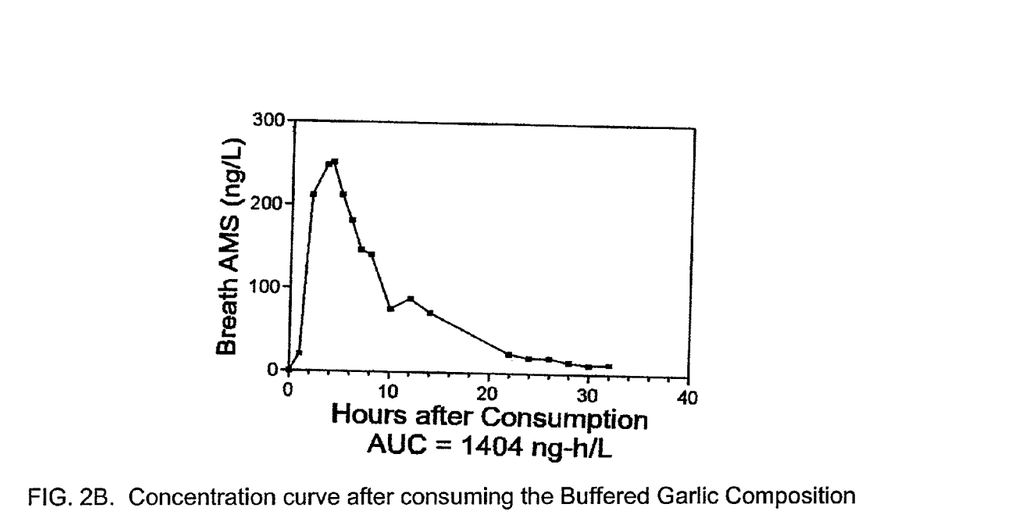

In one preferred embodiment, the alkalizing compositions may be used to prepare buffered garlic compositions. The buffered garlic compositions produced in accordance with the methods disclosed herein are characterized as retaining a high amount of allicin that is comparable to the amount found in fresh macerated garlic. FIGS. 2A and 2B show the allicin bioavailability from fresh garlic and the allicin bioavailability from the buffered garlic compositions, respectively.

The bioavailability of allicin in the buffered garlic compositions is due, in part, to the presence of the alkalizing composition. This is because the alkalizing compositions at least partially neutralizes the stomach acids which would otherwise deactivate allinase.

Figure 3:
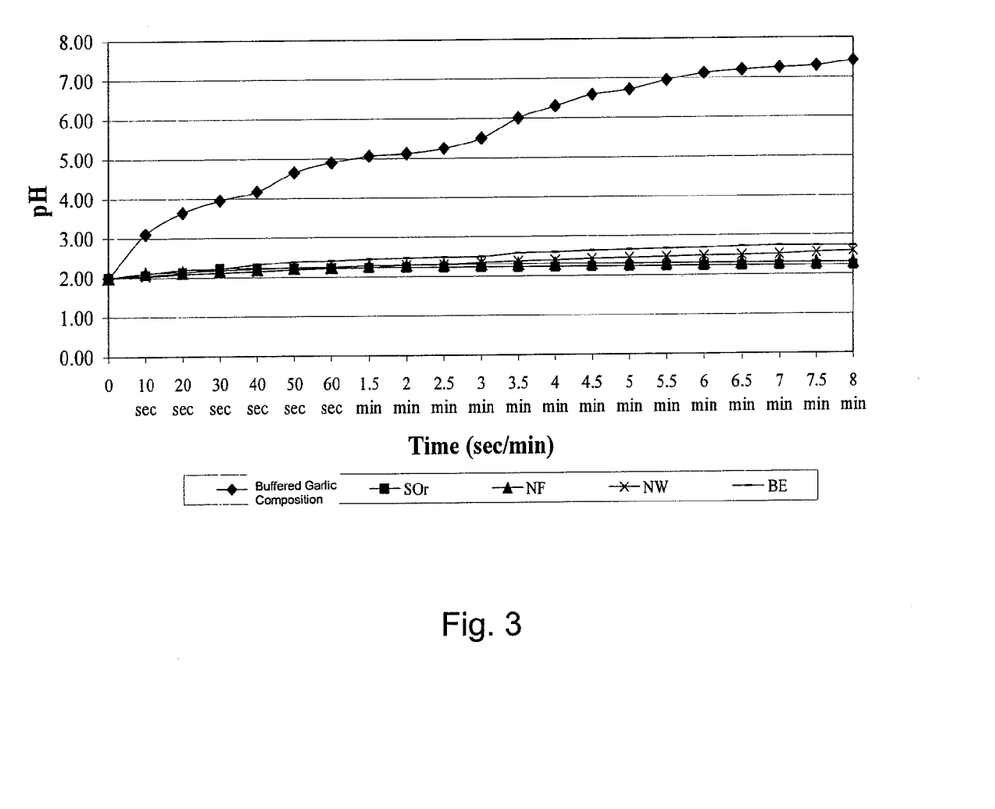
FIG. 3 compares the buffering effectiveness over time of the neutralization of 0.017 M HCl (pH 2.0) by the buffered garlic compositions with various garlic supplements.

FIG. 3 compares the buffering effectiveness of the buffered garlic compositions with various garlic supplements in neutralizing 0.017 M HCl (pH 2.0). This figure shows that the superior buffering action of buffered garlic compositions disclosed herein as compared to other known garlic supplements.

In one aspect of the preferred embodiment, the alkalizing composition is provided as an aqueous solution that is directly applied onto fresh garlic. In another aspect of the preferred embodiment, the alkalizing composition is provided as an granular agglomerate that is dry blended with agglomerated garlic powder.

In another preferred embodiment, the alkalizing compositions may be used in processes to enhance the flavor of fruits and vegetables. The application of the alkalizing compositions to fruits and vegetables modifies their natural pH and has been found to improve their flavor, color, and texture.

In one aspect of this preferred embodiment, the alkalizing composition provided in an aqueous solution. The fruits and vegetables are either dipped in or sprayed with the aqueous solution and then partially dried and frozen.

The following examples further illustrate the embodiments disclosed herein. These examples are provided only for purpose of illustrating the preferred embodiments of the invention and do not limit the invention in any manner.

Example 1

Alkalizing Compositions

The alkalizing compositions disclosed herein may be formulated as a antacid or as a nutritional and/or dietary supplement for reducing gastric distress resulting from excess stomach acid.

The alkalizing compositions disclosed herein may also be used in various processes for treating fresh or dried garlic and for enhancing the flavor of fruits and vegetables.

The following alkalizing compositions are suitable for use in the formulations and methods disclosed herein and in the Examples that follow:

| Formulation #1 | |
|---|---|
| Ingredients | % by weight |
| calcium carbonate | 79.08 |
| magnesium hydroxide | 7.77 |
| DC ascorbic acid | 5.00 |
| gum acacia | 4.76 |
| potassium hydroxide | 1.99 |
| dicalcium phosphate | 1.40 |

In one preferred embodiment, the alkalizing composition comprises from about 50% to about 99%, preferably from about 60% to about 90%, and more preferably from about 70% to about 85% by weight calcium carbonate, from about 0.01% to about 10%, preferably from about 0.01% to about 8%, and more preferably from about 5% to about 8% by weight magnesium hydroxide, from about 0.01% to about 10%, preferably from about 0.01% to about 8%, and more preferably from about 0.01% to about 6% by weight ascorbic acid, from about 0.01% to about 10%, preferably from about 0.01% to about 8%, and more preferably from about 0.01% to about 6% by weight gum acacia, from about 0.01% to about 10%, preferably from about 0.01% to about 8%, and more preferably from about 0.01% to about 6% by weight potassium hydroxide, and from about 0.01% to about 10%, preferably from about 0.01% to about 8%, and more preferably from about 0.01% to about 6% by weight dicalcium phosphate.

| Formulation #2 | |
|---|---|
| Ingredients | % by weight |
| calcium carbonate | 80.48 |
| magnesium hydroxide | 7.77 |
| DC ascorbic acid | 5.00 |
| gum acacia | 4.76 |
| potassium hydroxide | 1.99 |

In one preferred embodiment, the alkalizing composition comprises from about 50% to about 99%, preferably from about 60% to about 90%, and more preferably from about 70% to about 85% by weight calcium carbonate, from about 0.01% to about 10%, preferably from about 0.01% to about 8%, and more preferably from about 5% to about 8% by weight magnesium hydroxide, from about 0.01% to about 10%, preferably from about 0.01% to about 8%, and more preferably from about 0.01% to about 6% by weight ascorbic acid, from about 0.01% to about 10%, preferably from about 0.01% to about 8%, and more preferably from about 0.01% to about 6% by weight gum acacia, and from about 0.01% to about 10%, preferably from about 0.01% to about 8%, and more preferably from about 0.01% to about 6% by weight potassium hydroxide.

| Formulation #3 | |
| --- | --- |
| Ingredients | % by weight |
| calcium carbonate | 82.00 |
| sodium hydroxide | 7.50 |
| dicalcium phosphate | 2.00 |
| potassium hydroxide | 2.05 |
| potassium bicarbonate | 1.65 |
| gum acacia | 4.80 |

| Formulation #4 | |
| --- | --- |
| Ingredients | % by weight |
| calcium carbonate | 82.00 |
| sodium hydroxide | 7.00 |
| dicalcium phosphate | 2.00 |
| potassium hydroxide | 2.00 |
| potassium bicarbonate | 3.00 |
| gum acacia | 4.00 |

In another preferred embodiment, the alkalizing composition comprises from about 50% to about 99%, preferably from about 60% to about 90%, and more preferably from about 70% to about 85% by weight calcium carbonate, from about 0.01% to about 10%, preferably from about 2% to about 10%, and more preferably from about 5% to about 9% by weight sodium hydroxide, from about 0.01% to about 10%, preferably from about 0.01% to about 8%, and more preferably from about 0.01% to about 4% by weight dicalcium phosphate, from about 0.01% to about 10%, preferably from about 0.01% to about 8%, and more preferably from about 0.01% to about 4% by weight potassium hydroxide, from about 0.01% to about 10%, preferably from about 0.01% to about 8%, and more preferably from about 0.01% to about 4% by weight potassium bicarbonate, from about 0.01% to about 10%, preferably from about 0.1% to about 8%, and more preferably from about 0.01% to about 6% by weight gum acacia.

| Formulation #5 | |
| --- | --- |
| Ingredients | % by weight |
| calcium carbonate | 84.00 |
| potassium hydroxide | 4.50 |
| gum acacia | 4.50 |
| potassium bicarbonate | 2.90 |
| dicalcium phosphate | 2.90 |
| tricalcium phosphate | 1.20 |

In yet another preferred embodiment, the alkalizing composition comprises from about 50% to about 99%, preferably from about 60% to about 90%, and more preferably from about 75% to about 90% by weight calcium carbonate, from about 0.01% to about 10%, preferably from about 0.01% to about 8%, and more preferably from about 0.01% to about 6% by weight potassium hydroxide, from about 0.01% to about 10%, preferably from about 0.01% to about 6%, and more preferably from about 0.01% to about 4% by weight dicalcium phosphate, from about 0.01% to about 10%, preferably from about 0.01% to about 6%, and more preferably from about 0.01% to about 4% by weight tricalcium phosphate, and from about 0.01%, preferably from about 0.01% to about 6%, and more preferably from about 0.01% to about 4% to about 10% by weight potassium bicarbonate.

The alkalizing compositions may be produced as a granulated, agglomerate compound by milling, blending and spray drying the ingredients in a Shugi agglomerating system. The Shugi agglomerating system is a commercially available system that has been designed to agglomerate minerals to USP and pharmaceutical standards. It is designed to properly mix and agglomerate various ingredients with different molecular weights into a uniform granule.

The ingredients are first milled to a fine powder. The fine powder is then heated to 30° to 39° C. and pressure sprayed into environment having a relative humidity of from about 9.0% to about 15.0%. The fine powder is then sprayed with a solution of gum acacia to achieve a uniform granule that is free-flowing, non-dusting, and highly compressible. Gum acacia aids in providing uniform finished granules.

The resulting granulated alkalizing compositions have a pH in the range of from about 5.0 to about 13.0, preferably about 6.5 to about 11.5, and more preferably from about 8.0 to about 10.0.

Example 2

Methods of Treating Fresh and Dried Garlic with the Alkalizing Compositions

The alkalizing compositions disclosed herein may be used in connection with methods for treating fresh and dried garlic to create a buffered garlic composition suitable consumption.

In one preferred embodiment, the methods disclosed herein are used in connection with fresh garlic. In this preferred embodiment, the garlic is selected in accordance with its ability to yield from about 4,000 mcg/g to over 15,000 mcg/g allicin.

The selected garlic is stored at about 40° F. to about 50° F. to preserve allinase and other enzymes that are responsible for producing allicin. The garlic is then dried to about 3.0% to about 6.5% max. by weight water and the presence of key markers compounds in the garlic, such as allicin, alliin, thiosulfinates, and s-allyl gamma-gluatmyl-cysteine sulfur, are verified by HPLC. Once the presence of the key marker compounds are verified, the selected garlic is prepared for the treatment and drying processes.

The selected fresh garlic bulbs are cracked, peeled and trimmed to remove excess root plate and any damage from harvesting. The whole garlic cloves are then washed in a solution of water containing from about 0.01% to about 0.5% paracetic acid to eliminate any harmful microorganisms, such as surface yeast, mold, bacteria and to facilitate the retardation of the enzymatic activity of the allinase.

The whole garlic cloves are then washed in chlorinated water and cut into thin slices. In a preferred embodiment, the garlic cloves are sliced in approximately 0.01 mm slices with a suitable commercial slicer. The thin garlic slices are then rinsed in chlorinated water to remove surface sugars, activated enzymes, lachrymators and other compounds that are created during the slicing of the whole garlic cloves.

The thin garlic slices are then dipped or sprayed with a solution of about 0.1% to about 0.5% citric acid in water to deactivate the allinase enzymes and to retard allicin formation. The citric acid solution preferably has a pH of about 3.1 to about 3.8.

The treated garlic slices are then sprayed with or dipped into a solution of the alkalizing composition. In one embodiment, a solution of about 0.002% to about 0.9% by weight of the following alkalizing composition may be used:

| Formulation #6 | |
|---|---|
| Ingredients | % by weight |
| calcium carbonate | 80.48 |
| magnesium hydroxide | 7.77 |
| DC acorbic acid | 5.00 |
| gum acacia | 4.77 |
| potassium hydroxide | 1.98 |

In accordance with in preferred embodiment, the alkalizing composition may comprise from about 50% to about 99%, preferably from about 60% to about 95%, and more preferably from about 70% to about 90% by weight calcium carbonate, from about 0.01% to about 10%, preferably from about 0.01% to about 8%, and more preferably from about 4% to about 8% by weight magnesium hydroxide, from about 0.01% to about 10%, preferably from about 0.01% to about 8%, and more preferably from about 0.01% to about 6% by weight ascorbic acid, from about 0.01% to about 10%, preferably from about 0.01% to about 8%, and more preferably from about 0.01% to about 6% by weight gum acacia, from about 0.01% to about 10%, preferably from about 0.01% to about 6%, and more preferably from about 0.01% to about 4% by weight potassium hydroxide.

In another preferred embodiment, the following solution may be sprayed directly onto the treated garlic slices:

| Formulation #7 | |
|---|---|
| Ingredients | % by weight |
| deionized water | 77.00 |
| calcium carbonate | 20.02 |
| potassium hydroxide | 1.50 |
| potassium bicarbonate | 1.00 |
| dicalcium phosphate | 0.48 |

Accordingly, the alkalizing composition may be provided in an aqueous solution comprising from about 50% to about 99%, preferably from about 60% to about 90%, and more preferably from about 70% to about 80% by weight water, from about 10% to about 40%, preferably from about 15% to about 35%, and more preferably from about 20% to about 30% by weight calcium carbonate, from about 0.01% to about 10%, preferably from about 0.01% to about 6%, and more preferably from about 0.01% to about 4% by weight potassium hydroxide, from about 0.01% to about 10%, preferably from about 0.01% to about 6%, and more preferably from about 0.01% to about 4% by weight potassium bicarbonate, and from about 0.01% to about 10%, preferably from about 0.01% to about 6%, and more preferably from about 0.01% to about 4% by weight dicalcium phosphate.

The garlic slices are then conveyed to a tunnel dryer, bin dryer, or continuous belt dryer and dried to about 3.5% to about 6.5% by weight water. The finished product is then milled into a powder or granules in accordance with methods and processes known to one of ordinary skill in the art.

The finished garlic powder or granules are then assayed for its allicin and total sulfur content using HPLC and standardized LECO sulfur test methods.

In another preferred embodiment, the buffered garlic compositions may be produced by dry-blending dehydrated high allicin garlic powder and the alkalizing compositions disclosed herein. In accordance with this preferred embodiment, the dehydrated garlic powder is heated from about 30° C. to about 39° C. and injected into a humidified atmosphere of about 9.0% water in a filter-mat batch dryer. The garlic powder is then agglomerated using a mixture of about 50% by weight gum acacia and 50% by weight guar gum at about 3.5% by weight of the total batch formula to about 7.5% in deionized water that is treated with about 0.4% to about 0.8% citric acid to achieve a pH of about 3.2 to about 3.9 to stabilize the garlic enzymes.

The finished agglomerate of the garlic granules are then blended with the alkalizing compositions to achieve the desired pH of about 5.4 to about 8.0. The resultant agglomerate of the garlic granules and the alkalizing composition is from about 77% to about 81% by weight of garlic and from about 19% to about 23% by weight alkalizing composition and preferably provides an allicin yield of greater than 4,000 mcg/g in 0.017 M HCl solution having a pH of about 2.0 to about 3.0.

The following alkalizing compositions may be blended with the dehydrated garlic powder or prepared in an aqueous solution and to treat fresh garlic to provide a high allicin yield garlic composition:

| Formulation #8 | |
|---|---|
| Ingredients | % by weight |
| calcium carbonate | 88.08 |
| potassium hydroxide | 6.00 |
| potassium bicarbonate | 4.00 |
| dicalcium phosphate | 1.92 |

In one preferred embodiment the alkalizing composition comprises from about 50% to about 99%, preferably from about 60% to about 95%, and more preferably from about 70% to about 90% by weight calcium carbonate, from about 0.01% to about 10%, more preferably from about 2% to about 8%, and more preferably from about 4% to about 7% by weight potassium hydroxide, from about 0.01% to about 10%, preferably from about 0.01% to about 8%, and more preferably from about 0.01% to about 6% by weight potassium bicarbonate, and from about 0.01% to about 5%, preferably from about 0.01% to about 4%, and more preferably from about 0.01% to about 3% by weight dicalcium phosphate.

| Formulation #9 | |
|---|---|
| Ingredients | % by weight |
| calcium carbonate | 80.48 |
| magnesium hydroxide | 7.77 |
| gum acacia | 4.77 |
| DC acorbic acid | 3.00 |
| dicalcium phosphate | 2.00 |
| potassium hydroxide | 1.98 |

| Formulation #10 | |
|---|---|
| Ingredients | % by weight |
| calcium carbonate | 79.40 |
| magnesium hydroxide | 7.20 |
| gum acacia | 4.77 |
| DC acorbic acid | 3.00 |
| dicalcium phosphate | 2.00 |
| potassium hydroxide | 1.98 |
| potassium bicarbonate | 1.65 |

In another preferred embodiment, the alkalizing composition comprises from about 50% to about 99% by weight calcium carbonate, preferably from about 60% to about 95% by weight, and more preferably from about 70% to about 90% by weight calcium carbonate, from about 0.01% to about 10%, preferably from about 0.01% to about 8%, and more preferably from about 5% to about 8% by weight magnesium hydroxide, from about 0.01% to about 10% by weight, preferably from about 0.01% to about 8%, and more preferably from about 0.01% to about 6% by weight gum acacia, from about 0.01% to about 10%, preferably from about 0.01% to about 8%, and more preferably from about 0.01% to about 5% by weight ascorbic acid, from about 0.01% to about 10%, preferably from about 0.01% to about 6%, and more preferably from about 0.01% to about 4% by weight dicalcium phosphate, and from about 0.01% to about 10%, preferably from about 0.01% to about 6%, and more preferably from about 0.01% to about 4% by weight potassium hydroxide.

| Formulation #11 | |
|---|---|
| Ingredients | % by weight |
| calcium carbonate | 82.50 |
| magnesium hydroxide | 7.00 |
| dicalcium phosphate | 2.00 |
| potassium hydroxide | 2.00 |
| potassium bicarbonate | 1.50 |
| gum acacia | 5.00 |

In yet a further preferred embodiment, the alkalizing composition comprises from about 50% to about 99%, preferably from about 60% to about 90%, and more preferably from about 70% to about 85% by weight calcium carbonate, from about 0.01% to about 10%, preferably from about 0.01% to about 8%, and more preferably from about 5% to about 8% by weight magnesium hydroxide, from about 0.01% to about 10%, preferably from about 0.01% to about 8%, and more preferably from about 0.01% to about 5% by weight dicalcium phosphate, from about 0.01% to about 10%, preferably from about 0.01% to about 6%, and more preferably from about 0.01% to about 4% by weight potassium hydroxide, from about 0.01% to about 10%, preferably from about 0.01% to about 6%, and more preferably from about 0.01% to about 4% by weight potassium bicarbonate, from about 0.01% to about 10%, preferably from about 0.01% to about 8%, and more preferably from about 0.01% to about 6% by weight gum acacia. The alkalizing composition may further comprise a vitamin, such as ascorbic acid.

The buffered garlic compositions prepared in accordance with the methods disclosed herein may be characterized as follows:

| Buffered Garlic Composition #1 | |
|---|---|
| Ingredients | % by weight |
| garlic | 77.00 |
| calcium carbonate | 19.00 |
| potassium hydroxide | 1.50 |
| magnesium hydroxide | 1.50 |
| potassium bicarbonate | 0.50 |
| dicalcium phosphate | 0.50 |

In one preferred embodiment, the buffered garlic composition may comprise from about 50% to about 99%, preferably from about 60% to about 95%, and more preferably from about 70% to about 80% by weight garlic, from about 1% to about 40%, preferably from about 10% to about 30%, and more preferably from about 15% to about 25% by weight calcium carbonate, from about 0.01% to about 10%, preferably from about 0.01% to about 6%, and more preferably from about 0.01% to about 4% by weight potassium hydroxide, from about 0.01% to about 10%, preferably from about 0.01% to about 6%, and more preferably from about 0.01% to about 4% by weight magnesium hydroxide, from about 0.01% to about 10%, preferably from about 0.01% to about 6%, and more preferably from about 0.01% to about 2% by weight potassium bicarbonate, and from about 0.01% to about 10%, preferably from about 0.01% to about 6%, and more preferably from about 0.01% to about 2% by weight dicalcium phosphate.

| Buffered Garlic Composition #2 | |
|---|---|
| Ingredients | % by weight |
| Garlic | 75.00 |
| calcium carbonate | 20.00 |
| sodium hydroxide | 2.00 |
| potassium hydroxide | 1.50 |
| potassium bicarbonate | 1.00 |
| dicalcium phosphate | 0.50 |

In one preferred embodiment, the buffered garlic composition may comprise from about 50% to about 99%, preferably from about 60% to about 95%, and more preferably from about 70% to about 80% by weight garlic, from about 1% to about 40%, preferably from about 10% to about 30%, and more preferably from about 15% to about 25% by weight calcium carbonate, from about 0.01% to about 10%, preferably from about 0.01% to about 6%, and more preferably from about 0.01% to about 4% by weight potassium hydroxide, from about 0.01% to about 10%, preferably from about 0.01% to about 6%, and more preferably from about 0.01% to about 4% by weight sodium hydroxide, from about 0.01% to about 10%, preferably from about 0.01% to about 6%, and more preferably from about 0.01% to about 2% by weight potassium bicarbonate, and from about 0.01% to about 10%, preferably from about 0.01% to about 6%, and more preferably from about 0.01% to about 2% by weight dicalcium phosphate.

| Buffered Garlic Composition #3 | |
| --- | --- |
| Ingredients | % by weight |
| garlic | 23.00 |
| calcium carbonate | 63.00 |
| potassium hydroxide | 2.50 |
| magnesium hydroxide | 7.50 |
| potassium bicarbonate | 2.00 |
| dicalcium phosphate | 2.00 |

| Buffered Garlic Composition #4 | |
| --- | --- |
| Ingredients | % by weight |
| garlic | 18.00 |
| calcium carbonate | 66.80 |
| magnesium hydroxide | 7.20 |
| potassium hydroxide | 2.50 |
| potassium bicarbonate | 2.80 |
| dicalcium phosphate | 2.70 |

In one preferred embodiment, the buffered garlic composition may comprise from about 1% to about 40%, preferably 10% to about 30%, and more preferably from about 15% to about 25% by weight garlic, from about 40% to about 90%, preferably from about 50% to about 80%, and more preferably from about 60% to about 70% by weight calcium carbonate, from about 0.01% to about 10%, preferably from about 0.01% to about 8%, and more preferably from about 0.01% to about 6% by weight potassium hydroxide, from about 0.01% to about 10%, preferably from about 2% to about 10%, and more preferably from about 4% to about 8% by weight magnesium hydroxide, from about 0.01% to about 10% preferably from about 0.01% to about 8%, and more preferably from about 0.01% to about 6% by weight potassium bicarbonate, and from about 0.01% to about 10% preferably from about 0.01% to about 8%, and more preferably from about 0.01% to about 6% by weight dicalcium phosphate.

Example 3

Method of Enhancing the Flavor of Reduced Moisture Fruits and Vegetables

The alkalizing compositions disclosed herein may also be used in connection with methods to enhance the flavor of fruits and vegetables. The method generally comprises the steps of applying the alkalizing solution to the fruits and vegetables and then partially drying and quick-freezing the fruits and vegetables.

The step of applying a solution of the alkalizing solution modifies the natural pH of the fruits and vegetables and improves flavor, color, and texture of the fruits and vegetables. The modification of the acids contained in the fruits and vegetables at least partially neutralizes the stronger flavors and allows for the weaker flavors to be expressed.

The step of applying the alkalizing solution may be accomplished by any number of methods known to one of ordinary skill in the art, including dipping the fruits and vegetables into the alkalizing solution or spraying the alkalizing solution onto the fruits and vegetables.

In embodiments where the method includes spraying the alkalizing solution onto the fruits and vegetables, the application rate and the precise alkalizing solutions used may depend on the precise fruits and/or vegetables selected and the size of the fruit and/or vegetable pieces. The precise alkalizing solution used, the application rate of the alkalizing solution, and the sizes to which the fruits and vegetables are cut are based on the solids content and the pH of the fruits and/or vegetable, which is determined from laboratory testing using a microwave solids analyzer.

Solutions are prepared to meet the desired finished product attributes for color, flavor, texture, solids, pH, total acidity, and synersis. The solution is prepared with a pH of approximately 10 and it can be applied at different rates by adjusting the spray pressure and belt speeds for greater absorption.

In another preferred embodiment, the solution utilizes a spray system to lightly coat the individual fruit and vegetable pieces at a concentration of from about 0.006% to about 1.5% by weight of the alkalizing composition.

In yet another embodiment, the alkalizing compositions comprise calcium carbonate, magnesium hydroxide, DC ascorbic acid, gum acacia, potassium hydroxide, and dicalcium phosphate. Optionally, the alkalizing compositions may contain vitamin $D_3$ to help the mineral absorption into the fruits and vegetables. The following formulations may be used to produce suitable alkalizing compositions for use in connection with the methods disclosed herein:

| Formulation #12 | |
| --- | --- |
| Ingredients | % by weight |
| calcium carbonate | 79.08 |
| magnesium hydroxide | 7.77 |
| DC ascorbic acid | 5.00 |
| gum acacia | 4.76 |
| potassium hydroxide | 1.99 |
| dicalcium phosphate | 1.40 |

In another embodiment, the alkalizing compositions comprise calcium carbonate, magnesium hydroxide, DC ascorbic acid, gum acacia, potassium hydroxide, and optionally vitamin $D_3$. The following formulations may be used to produce suitable alkalizing compositions for use in connection with the methods disclosed herein:

| Formulation #13 | |
| --- | --- |
| Ingredients | % by weight |
| calcium carbonate | 80.48 |
| magnesium hydroxide | 7.77 |
| DC ascorbic acid | 5.00 |
| gum acacia | 4.76 |
| potassium hydroxide | 1.99 |

The calcium carbonate, magnesium hydroxide, and potassium hydroxide is used to alter the pKa and therefore the pH of the fruits and vegetables. Moreover, these compounds are used to neutralize the bitter taste of calcium chloride that is typically found in frozen or thermally processed fruits and vegetables. Calcium chloride is typically sprayed on certain fruits and vegetables to stabilize pectin and to make a firmer product. The DC ascorbic acid and vitamin $D_3$ in the alkalizing compositions function to improve the absorption of calcium carbonate, magnesium hydroxide and potassium hydroxide into the fruits and vegetables to improve texture and to the acid/base balance.

The solution containing the alkalizing composition is continuously agitated to ensure uniformity and is sprayed onto the fruits and vegetables to achieve a 0.7 to 1.5% by weight of the alkalizing composition in an aqueous solution.

The step of partial drying the fruits and vegetables removes free moisture and concentrates the natural flavor. Because the water content in the fruits and vegetables are reduced, the formation of ice crystals that cause damage to cell structures will also be reduced.

In one embodiment, the step of partially drying the fruits and vegetables include utilizing a belt dryer, a bin dryer, or a tray dryer to reduce the moisture content of the fruits and vegetables from about 10% to about 50% by weight of the treated fruits and vegetables.

The fruits and vegetables are then fed into a fluid bed freezer with a temperature of between about 0° F. to about −20° F. to individually quick-freeze the fruits and vegetables. The partially-dried fruits and vegetables are then passed through a specialized hot air pasteurization unit to kill harmful bacteria and other pathogens.

Example 4

Electrolytic Beverage

The alkalizing composition disclosed herein may also be combined with water to produce an electrolytic or sports beverage. The beverage may be consumed after strenuous physical exercise to replenish electrolytes, to invigorate muscles, and to reduce gastric distress resulting from excess stomach acid.

In one preferred embodiment, the pKa of the beverage is from about 5.5 to about 12.0. In a preferred embodiment, the pKa of the beverage is from about 7.0 to about 10.5. In a particularly preferred embodiment, the pKa of the beverage is from about 8.5 to about 9.0.

The following is an example of an electrolytic beverage produced in accordance with the methods disclosed herein:

| Formulation #14 | |
| --- | --- |
| Ingredients | % by weight |
| deionized water | 75.00 |
| calcium carbonate | 20.07 |
| concentrated sea minerals | 2.07 |
| magnesium hydroxide | 1.96 |
| potassium hydroxide | 0.50 |
| dicalcium phosphate | 0.40 |

In one embodiment, the beverage comprises from about 50% to about 99%, preferably from about 60% to about 90%, and more preferably from about 70% to about 80% by weight water, from about 5% to about 40%, preferably from about 10% to about 30%, and more preferably from about 15% to about 25% by weight calcium carbonate, from about 0.01% to about 10%, preferably from about 0.01% to about 8%, and more preferably from about 0.01% to about 6% by weight concentrated sea minerals, from about 0.01% to about 10%, preferably from about 0.01% to about 8%, and more preferably from about 0.01% to about 6% by weight magnesium hydroxide, from about 0.01% to about 10%, preferably from about 0.01% to about 8%, and more preferably from about 0.01% to about 6% by weight potassium hydroxide, from about 0.01% to about 10%, preferably from about 0.01% to about 8%, and more preferably from about 0.01% to about 6% by weight dicalcium phosphate.

The invention described and claimed herein is not to be limited in scope by the specific preferred embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims

The invention claimed is:

1. A buffered garlic composition comprising from about 50% to about 99% by weight garlic, from about 1% to about 40% by weight calcium carbonate, from about 0.01% to about 10% by weight potassium hydroxide, from about 0.01% to about 0.01% potassium bicarbonate, and from about 0.01% to about 10% by weight dicalcium phosphate.

2. The buffered garlic composition of claim 1 further comprising magnesium hydroxide.

3. The buffered garlic composition of claim 2, wherein the garlic is high-allicin garlic powder.

4. The buffered garlic composition of claim 3, wherein the composition comprises from about 0.01% to about 10% by weight magnesium hydroxide.

5. The buffered garlic composition of claim 2 further comprising sodium hydroxide.

6. The buffered garlic composition of claim 5, wherein the garlic is high-allicin garlic powder.

7. The buffered garlic composition of claim 1 wherein when delivered to the stomach, the bioavailability of allicin in the stomach is higher than if the garlic were delivered to the stomach without the buffering components calcium carbonate, potassium hydroxide, potassium bicarbonate, and dicalcium phosphate.

8. The buffered garlic composition of claim 1 wherein the bioavailability of allicin the stomach is comparable to the bioavailability of allicin in fresh macerated garlic.

9. A buffered garlic composition comprising garlic, calcium carbonate, potassium hydroxide, potassium bicarbonate, dicalcium phosphate, sodium hydroxide and magnesium hydroxide, wherein the garlic is high-allicin garlic powder, wherein the composition comprises from about 50% to about 99% by weight garlic, from about 1% to about 40% by weight calcium carbonate, from about 0.01% to about 10% by weight potassium hydroxide, from about 0.01% to about 10% by weight sodium hydroxide, from about 0.01% to about 10% by weight potassium bicarbonate, and from about 0.01% to about 10% by weight dicalcium phosphate.

10. A buffered garlic composition comprising garlic, calcium carbonate, potassium hydroxide, potassium bicarbonate, dicalcium phosphate, and magnesium hydroxide, wherein the composition comprises from about 1% to about 40% by weight garlic, from about 40% to about 90% by weight calcium carbonate, from about 0.01% to about 10% by weight potassium hydroxide, from about 0.01% to about 10% by weight magnesium hydroxide, from about 0.01% to about 10% by weight potassium bicarbonate, and from about 0.01% to about 10% by weight dicalcium phosphate.

* * * * *